United States Patent [19]
Ritscher et al.

[11] Patent Number: 5,359,109
[45] Date of Patent: Oct. 25, 1994

[54] SURFACE-ACTIVE SILOXANE COATING COMPOUNDS AND THEIR USE IN COATINGS

[75] Inventors: James S. Ritscher; James D. Reedy, both of Marietta, Ohio; Kenneth W. Hartman, Middlebourne, W. Va.

[73] Assignee: OSi Specialties, Inc., Danbury, Conn.

[21] Appl. No.: 78,590

[22] Filed: Jun. 16, 1993

[51] Int. Cl.$^5$ .............................................. C07F 7/08
[52] U.S. Cl. .................................................. 556/434
[58] Field of Search ........................................ 556/434

[56] References Cited

U.S. PATENT DOCUMENTS

| | | | |
|---|---|---|---|
| 2,507,519 | 5/1950 | Goodwin | 556/434 X |
| 3,122,522 | 2/1964 | Brown et al. | 260/46.5 |
| 3,175,993 | 3/1965 | Weyenberg | 260/46.5 |
| 3,419,423 | 12/1968 | Quaal | 117/161 |
| 3,427,338 | 2/1969 | Frye | 260/448.2 |
| 3,509,081 | 4/1970 | Gignac | 260/18 |
| 4,200,664 | 4/1980 | Young et al. | 427/4 |
| 4,499,150 | 2/1985 | Dowbenko et al. | 428/447 |
| 4,579,964 | 4/1986 | Totten et al. | 556/434 |
| 4,743,474 | 5/1988 | Homan | 427/387 |
| 4,772,675 | 9/1988 | Klosowski et al. | 556/434 X |
| 4,962,174 | 10/1990 | Bilgrien et al. | 528/15 |
| 5,068,277 | 11/1991 | Vukov et al. | 524/441 |
| 5,272,243 | 12/1993 | Nakashima et al. | 556/434 X |

OTHER PUBLICATIONS

Sheludyakov, V. D. et al., "Side Reactions in the Hydrosilylation of Vinylsilanes in the Presence of Speier's Catalyst," *J. General Chemistry USSR*, 55, 1594 (1985).
Sheludyakov, V. D. et al., "Some Features of the Hydrosilylation of Vinylsilanes," *J. General Chemistry USSR*, 55, 1372 (1985).
Souchek, I. et al., "The Reactivity of Methylvinylsiloxanes in Hydride Addition Reactions," *Proceedings, Academy of Science USSR*, 222, 305 (1975).
Bazant, V., "Organosilicon Compounds by Hydrosilylation," *Chemical Abstracts*, 80, (1974), 83225c.
Gorshkov, A. V., "Rubber Stock," *Chemical Abstracts*, 103, (1985), 161677m.
Andrianov, K. A. et al., "Hydride Addition of Pentamethyldisiloxane to Heptamethylvinylcyclotetrasiloxane in the Presence of Complex Compounds of Group VII Metals: Catalysis by Complex Compounds of Metals," *J. General Chemistry USSR*, 45, 2176 (1975).
Frye, C. L. et al., "Silicon-Functional 1,2,5-Oxadisilacyclopentane Heterocyclics," *J. Organic Chemistry*, 35, 2964 (1970).
Kopylov, V. M. et al., "Features of the Hydrosilylation of Polyfunctional Methylvinyl-and Methylhydrosiloxanes," English Version, *J. General Chemistry USSR*, 57, 998 (1987).
Pitt, C. G. et al., "Vinyl-hydrogen Ligand Exchange on Silicon," *J. Organometallic Chemistry* 7,525 (1967).

*Primary Examiner*—Paul F. Shaver
*Attorney, Agent, or Firm*—Andrew S. Reiskind

[57] ABSTRACT

The present invention provides a class of surface-active siloxane compounds each having a single reactive alkoxysilane moiety. The siloxane compounds are linear or cyclic and are reactive to moisture and to compositions having hydroxyl-functionality.

10 Claims, No Drawings

SURFACE-ACTIVE SILOXANE COATING COMPOUNDS AND THEIR USE IN COATINGS

FIELD OF THE INVENTION

The present invention relates to a class of surface-active siloxane compounds useful as surface coatings or useful for modifying surface coatings, such as, water repellent treatment or coatings on concrete, as additives in paints for metallic surfaces, and as hydrophobizing agents for inorganic fillers, and a method for preparing such surface-active siloxane compounds.

BACKGROUND OF THE INVENTION

There is an ongoing need to provide surface-active siloxane compounds for use in surface coatings to impart properties such as water repellency, spreadability, low friction coefficient, reduced brittleness, and high gloss to a variety of surfaces such as wood, metal, and concrete. There has correspondingly been a need to control these properties at a molecular level so that undesirable effects, such as excessive surface migration, poor paintablility, and areas of high localized cross-link density do not adversely affect a surface coating in its properties such as consistency, performance, or esthetic surface appearance.

Surprisingly, the present invention provides a class of siloxanes, each having a single reactive alkoxysilane moiety, which siloxanes are reactive to moisture and compositions having hydroxyl-functionality, including polymers of various kinds and inorganic substrates, such as silica fillers, and which siloxanes are stable and have long term storage capabilities.

SUMMARY OF THE INVENTION

The present invention provides a class of siloxane compounds having the general Formulae I (linear) or II (cyclic):

$$(RO)_x R^1_{3-x} SiR^2 SiX_y R^1_{3-y} \qquad (I)$$

(II)

$$(RO)_x R^1_{3-x} Si\underset{Q}{\overset{}{\mid}} O \left[ \underset{R}{\overset{R}{\mid}} Si \underset{R^1}{\overset{}{\mid}} O \right]_m$$

wherein
X is selected from the group consisting of $$-OSi(R)_3 \qquad (i)$$

and $$-(O-\underset{R}{\overset{R}{\underset{\mid}{Si}}}-)_q R \qquad (ii)$$

q has a value of 1 to 5;
R is an alkyl group having 1 to 6 carbon atoms;
$R^1$ is selected from the group consisting of
  (i) an alkyl group having 1 to 6 carbon atoms,
  (ii) an aryl group having 6 to 12 carbon atoms,
  (iii) an aralkyl group having 7 to 13 carbon atoms, and
  (iv) an alkaryl group having 7 to 13 carbon atoms;

$R^2$ is a linear or branched alkylene group having 2 to 12 carbon atoms;
Q is $R^1$ or X as defined herein;
m has a value of 3 to 5; and
x and y each has a value of 1 to 3.

DETAILED DESCRIPTION OF THE INVENTION

Surface-Active Siloxane Compounds

Preferably, in Formulae I and II, R and $R^1$ are each individually an alkyl group having 1 to 2 carbon atoms, i.e., methyl or ethyl; and, most preferably, R and $R^1$ are methyl groups. In Formulae I and II, preferably $R^2$ is an alkylene group ($-C_n H_{2n}-$) in which n has a value ranging from about 2 to 6; and, most preferably, n is 2. Preferably X is a trimethylsiloxy group when y has a value of 1 to 3 in Formula I. And in Formula II, preferably, Q is a methyl group; and m has a value of 3 or 4.

Process of Making the Surface Active Siloxane Compound

The surface-active siloxane compounds of Formula I of the present invention can be prepared by hydrosilation in accordance with either of the following reactions.

Reaction A $$HSiX_y R^1_{3-y} + (RO)_x R^1_{3-x} SiZ \rightarrow (RO)_x R^1_{3-x} SiR^2 SiX_y R^1_{3-y}$$

Reaction B $$ZSiX_y R^1_{3-y} + (RO)_x R^1_{3-x} SiH \rightarrow (RO)_x R^1_{3-x} SiR^2 SiX_y R^1_{3-y}$$

In Reactions A and B, R, $R^1$, $R^2$, X, y and x are as defined in Formula I. In Reactions A and B, Z is an alkenyl group, $-C_b H_{2b-1}$, wherein b has a value ranging from about 2 to 6 carbon atoms. The Z in the Reactions A and B forms $R^2$ of Formula I upon hydrosilation. Preferably, in the Reactions A and B, Z is a terminally unsaturated alkenyl group having 2 to 4 carbon atoms; and, most preferably, Z is a vinyl group ($-CH=CH_2$). Reaction A is the preferred process for producing the surface-active siloxane compounds of the present invention because the hydridosiloxane of Reaction A is more readily available than the vinyl siloxane employed in Reaction B.

Cyclic compounds $$ZSi\underset{Q}{\overset{}{\mid}} O \left[ \underset{R}{\overset{R^1}{\mid}} SiO \right]_m$$

and $$HSi\underset{Q}{\overset{}{\mid}} O \left[ \underset{R}{\overset{R^1}{\mid}} SiO \right]_m$$

which are reactants used to make the siloxanes of Formula II are readily commercially available and can be prepared as disclosed in *Bulletin of the Academy of Sci-* ences, USSR, 1975, pages 530–533 (English version). In general, the cyclic compounds set forth above are used in reactions analogous to Reactions A and B above, except that a cyclic hydridosiloxane is substituted for the linear hydridosiloxane of Reaction A or a cyclic vinylsiloxane is substituted for the linear vinyl-siloxane of Reaction B.

In general, the hydrosilation reactions of Reactions A and B are well known to those skilled in the art. Conditions under which hydrosilation reactions are performed with respect to pressure, temperature, amounts of reactants, catalyst, solvents, and equipment are likewise generally well known to those skilled in the art and can be varied widely while obtaining efficiency and good yield of product. In general, the hydrosilation reactions occur at ambient pressure and temperatures ranging from about 50° C. to 150° C. in the presence of a noble metal catalyst such as, for example, rhodium or platinum. Catalysis of hydrosilation reactions is well known to those skilled in the art, and noble metal catalysts are readily commercially available. For example, preferred catalysts which are readily commercially available include a 1,2-divinyltetramethyl disiloxane complex of platinum, often referred to as the Pt/Vi complex; platinum bis(acetylacetonate); and chloroplatinic acid, $H_2PtCl_6$. A most preferred catalyst is chloroplatinic acid.

Illustrative of the $(RO)_xR^1_{3-x}SiZ$ reactant which can be employed in Reaction A, for example, are the following alkenyl alkoxysilanes:

| | |
|---|---|
| $CH_2=CHSi(OMe)_3$ | |
| $CH_2=CHSiMe_2OMe$ | |
| $CH_2=CHSiMe(OEt)_2$ | |
| $CH_2=CHSiEt(OMe)_2$ | |
| $CH_2=CEtSiMe(OMe)_2$ | |
| $CH_2=CHCH_2SiMe(OMe)_2$ | |
| $CH_2=CHCH_2SiMe(OEt)_2$ | |
| $CH_2=CMeCH_2SiMe(OMe)_2$ | |
| $CH_3CH=CHSi(OMe)_3$ | |
| $CH_2=CH(CH_2)_4SiMe(OEt)_2$ | |
| $CH_2=CMeCH_2CH_2SiMe(OMe)_2$ | |
| $CH_2=C(C_4H_9)SiMe(OEt)_2$ | |
| $CH_2=CHSiMe(OMe)_2$ | |
| $CH_2=CHSi(OEt)_3$ | |
| $CH_2=CHSiMe_2OEt$ | |
| $CH_2=CMeSi(OMe)_3$ | |
| $CH_2=CHCH_2Si(OMe)_3$ | |
| $CH_2=CHCH_2SiMe_2OMe$ | |
| $CH_2=CMeCH_2Si(OMe)_3$ | |
| $CH_2=CMeCH_2SiMe_2OEt$ | |
| $CH_2=CH(CH_2)_3Si(OMe)_3$ | |
| $CH_2=CHCHMeCH_2Si(OMe)_3$ | |
| n-$C_4H_9CH=CHSi(OMe)_3$ | |
| $CH_2=CHSi(OPr-i)_3$, and the like. | |

Preferred $(RO)_xR^1_{3-x}SiZ$ reactants which can be employed in Reaction A include:

| | |
|---|---|
| $CH_2=CHSi(OMe)_3$ | $CH_2=CHSiMe(OMe)_2$ |
| $CH_2=CHSiMe_2OMe$ | $CH_2=CHSi(OEt)_3$ |
| $CH_2=CHSiMe(OEt)_2$ | $CH_2=CHSiMe_2OEt$ |
| $CH_2=CHCH_2SiMe(OMe)_2$ | $CH_2=CHSi(OPr-i)_3$ |
| $CH_2=CHCH_2SiMe(OEt)_2$ | $CH_2=CMeCH_2Si(OMe)_3$ |
| $CH_2=CHCH_2Si(OMe)_3$ | |

Most preferred $(RO)_xR^1_{3-x}SiZ$ reactants which can be employed in Reaction A include:

| | |
|---|---|
| $CH_2=CHSi(OMe)_3$ | $CH_2=CHSiMe(OMe)_2$ |

| | |
|---|---|
| $CH_2=CHSi(OEt)_3$ | $CH_2=CHSiMe(OEt)_2$ |

Illustrative of the $HSiX_yR^1_{3-y}$ reactant of Reaction A are the following hydridosiloxanes:

| | |
|---|---|
| $HSiMe_2OSiMe_3$ | $HSiMe(OSiMe_3)_2$ |
| $HSi(OSiMe_3)_3$ | $HSiMe_2(OSiMe_2)_2Me$ |
| $HSiMe_2(OSiMe_2)_5Me$ | $HSiMe(OSiMe_2OSiMe_3)_2$ |
| $HSiMe(OSiMe_3)OSiMe_2OSiMe_3$ | $HSiEt(OSiMe_3)_2$ |
| $H(C_6H_5)Si(OSiMe_3)_2$ | $HSiEt_2OSiEt_3$ |
| $HSiMe_2OSiMe_2C_6H_5$ | |

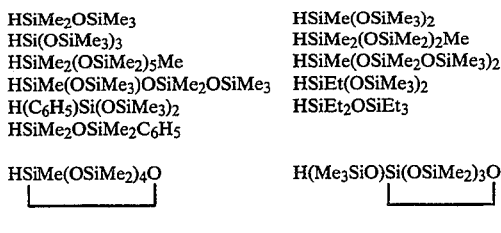

Preferably, the hydridosiloxane is one of:

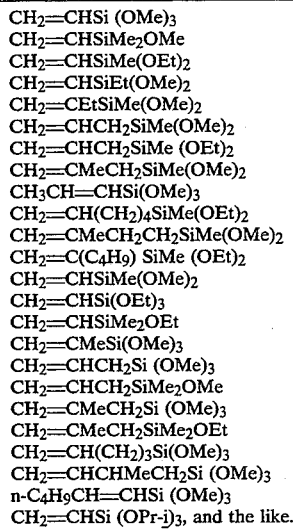

$HSi(OSiMe_3)_3$
$HSiMe(OSiMe_3)_2$
$HSiMe_2OSiMe_3$

Most preferably, the hydridosiloxane is $HSiMe(OSiMe_3)_2$.

The silicon compound reactants for Reaction B, namely $(RO)_xR^1_{3-x}SiH$ and $ZSiX_yR^1_{3-y}$, are, respectively, depicted by replacing the alkenyl groups Z of the alkenyl alkoxysilanes of Reaction A above with H and replacing the H groups of the hydridosiloxanes of Reaction A above with the alkenyl groups Z. For Reaction B, the most preferred reactants would be the series of hydridoalkoxysilanes, $(MeO)_xMe_{3-x}SiH$, where x is an integer of 1 to 3; and the vinylic siloxanes:

$CH_2=CHSiMe(OSiMe_3)_2$
$CH_2=CHSiMe_2OSiMe_3$
$CH=CHSi(OSiMe_3)_3$

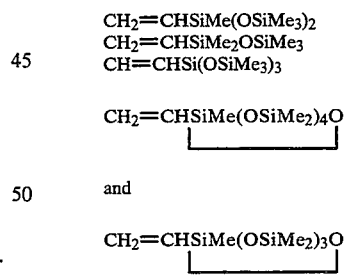

and

Accordingly, for example, $CH_2=CHSi(OMe)_3$ is reacted with $HSiMe(OSiMe_3)_2$ according to Reaction A; or, analogously, $(MeO)_3SiH$ is reacted with $CH_2=CHSiMe(OSiMe_3)_2$ according to Reaction B to give a structurally identical surface-active siloxane compound.

In the above illustrative reactants, Me represents a methyl group; Et represents an ethyl group; Pr represents a propyl group; and $C_6H_5$ represents a phenyl group. In the discussions which follow, both the hydridoalkoxysilanes and the hydridosiloxanes above may be referred to generically as hydridosilyl reactants; and the vinylalkoxysilanes and the vinylsiloxanes above may be referred to generically as vinyl silyl reactants.

While it is generally known that many hydrosilation processes are not narrowly critical in terms of the above-mentioned conditions, it is also known by those skilled in the art that hydrosilation reactions between alkenyl silicone compounds, particularly vinyl silyl compounds, and hydridosilyl compounds are complicated by two undesirable co-reactions, namely vinyl-hydrogen exchange reactions and the formation of internal adducts. These undesirable co-reactions are depicted in the following equations. It should be noted that when both vinyl-hydrogen exchange and internal adduct formation occur, a total of six structurally different products is formed. Such a complex reaction mixture requires purification, such as by distillation, when one or more of the products are contaminants which are detrimental to product performance.

Intended Reaction 1

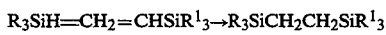

Vinyl-Hydrogen Exchange

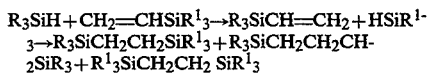

Intended Reaction 2

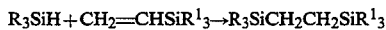

Internal Adduct $R_3SiH + CH_2 = CHSiR^1{}_3 \rightarrow R_3SiCH(CH_3)SiR^1{}_3$ In the present invention, the occurrence of vinyl-hydrogen exchange between, for example, $CH_2=CHSi(OMe)_3$ and $HSiMe(OSiMe_3)_2$ during hydrosilation, would lead to formation of $(MeO)_3SiCH_2CH_2Si(OMe)_3$ and $(Me_3SiO)_2SiMeCH_2CH_2SiMe(OSiMe_3)_2$, both of which lack the performance properties of the desired or intended product which is $(MeO)_3SiCH_2CH_2SiMe(OSiMe_3)_2$. From the perspective of product performance in the end use, the formation of internal adducts is a less significant problem, since both the requisite functionalities are present. Thus, the avoidance of vinyl-hydrogen exchange during the hydrosilation reactions and the minimization of formation of detrimental by-products is a desirable additional benefit of the present invention. That benefit is the increased yield of the desired surface-active compound by suppression of the yield of undesired by-products from the above co-reactions.

In the improved method of the present invention, the vinyl-hydrogen exchange reaction is minimized through the unexpected discovery of two factors. The first factor is that in either Reactions A or B, the vinylic silyl reactant is added to hydrosilyl reactant at reaction temperature, and not vice versa. The second factor is that the hydrosilation is conducted in the presence of an amine promoter capable of forming a weak complex with the active catalyst. Thus, for example, in Reaction A, the reaction of $(Me_3SiO)_2SiMeH$ with $CH_2=CHSi(OMe)_3$, is conducted by adding the vinylalkoxysilane to the hydridosiloxane in the presence of the catalyst and amine promoter. The yield of useful products (intended and internal adduct) was 84.77% with 2.63% of vinyl-hydrogen exchange products. When the reverse mode of addition was employed using the same catalyst and amine promoter, the yield of useful products was less, 75.01%, with a greater amount, 11.90%, of vinyl-hydrogen exchange products. Additionally, the latter reaction, conducted by adding the hydridosiloxane to the vinylsilane, was much slower, and could not be forced to completion. When the vinylalkoxysilane was added to the hydridosiloxane in the presence of the same catalyst (chloroplatinic acid), except that strongly complexing triphenylphosphine was used in place of the amine promoter, the yield of useful products was only 69.87% and 3.11% of vinyl-hydrogen exchange products.

By further comparison of this data, the present invention provides a product/by-product ratio of 32.2/1, while triphenylphosphine disclosed in U.S. Pat. No. 3,188,300 provides a product/by-product ratio of only 22.45/1 and reaction did not go to completion. A control reaction (no amine promoter, i.e., complexing agent) was conducted by adding the vinyl silane to the hydridosiloxane. The yield of useful products was 75.19% and 4.83% of vinyl-hydrogen exchange products, with a product/by-product ratio of 15.57/1. The results demonstrated that amine promoter increases both the total yield of useful products and the selectivity for such products.

In summary, it appears that amines capable of forming weak complexes with the catalyst promote both the increased yield of products and improved selectivity of intended product. In contrast, strongly complexing phosphines promote selectivity, but at the same time there is a reduction in the yield of the intended product. The mode of addition of reactants, that is adding the vinyl silyl reactant to the hydridosilyl reactant, and vice versa, affect both the yield of intended product and selectivity of intended product in the presence or absence of an amine promoter. Thus, the preferred process of the present invention is to employ Reaction A wherein the vinylic silane reactant is added to the hydridosiloxane reactant at reaction temperature, with the catalyst and amine promoter being present in the hydridosiloxane reactant.

The amine promoter employed in the method of the present invention is selected from the group consisting of phenothiazine, phenoxazine, diphenylamine, and N,N'-diphenyl-p-phenylenediamine or a carbon-alkylated derivative thereof. Phenothiazine and diphenylamine are particularly perferred as amine promoters in the method of the present invention. The amount of amine promoter ranges from about 0.001 to 1.0 weight percent based upon the total weight of reactants; preferably, from about 0.01 to 0.5 weight percent; and, most preferably, ranges from about 0.02 to 0.05 weight percent based upon the total weight of the reactants. Products of the present invention can be further purified, if desired, for example, by distillation. Generally, in accordance with the method of the present invention, purification is not necessary.

In the method of the present invention, the reaction temperature ranges from about 50° C. to 150° C., with 75° C. to 125° C. being preferred, and 90° C. to 125° C. being most preferred.

Methods of Using the Surface-Active Siloxane Compound

The surface-active siloxane compound of the present invention can be used as an additive in paints used to coat metallic surfaces, as an active agent in a water repellent coating for concrete surfaces, and as a hydrophobizing agent for inorganic fillers.

When the surface-active siloxane compound is employed as an additive in a paint, it is combined with the other ingredients of a paint formulation using conventional paint formulation procedures and techniques such as those disclosed in U.S. Pat. No. 4,499,150. In general, the surface-active siloxane compound can be incorporated into a paint for formulation as prepared or as purified. It is combined or mixed with the other ingredients in any order and in amounts ranging from about 0.1 to 20 weight percent; preferably, from about 1 to 10 weight percent based upon the total solids.

When the surface-active siloxane compound is employed as an active agent in a water repellent treatment or coating, as, for example, on concrete, it is typically diluted using a nonaqueous solvent which serves as a spreader or carrier. Such solvents can include, for example, a linear or branched alcohol having 1 to 6 carbon atoms, a ketone having 3 to 8 carbon atoms, an ester having 3 to 8 carbon atoms, an ether having 4 to 12 carbon atoms, a hydrocarbon having 8 to 16 carbon atoms, and mixtures thereof. The solvent and surface-active siloxane compound are combined, mixed, or blended to form the homogeneous solution using any means known to those skilled in the art. As an active agent in a water repellent treatment or coating, the surface-active siloxane compound is employed in an amount ranging from 5 to 50 weight percent based upon the total actives of the homogeneous solution. Alternatively, the surface-active compound can be part of an admixture using other well-known alkylalkoxysilanes. The water repellent treatment or coating can be applied by any conventional means such as, for example, brush or roller applicator, sprayer, or immersion bath.

When used as a hydrophobizing agent for inorganic filler, the surface-active siloxane compound can be used in the form of a homogeneous nonaqueous solution as described above, or as an aqueous emulsion to treat glass fibers, fabrics (natural and synthetic), fillers such as calcium carbonate, and pigments such as titanium dioxide. The homogeneous nonaqueous solution or aqueous emulsion is applied by any conventional means such as brush, roller applicator, sprayer, kiss roller or immersion bath.

Whereas the exact scope of the instant invention is set forth in the appended claims, the following specific examples illustrate certain aspects of the present invention and, more particularly, point out methods of evaluating the same. However, the examples are set forth for illustration only and are not to be construed as limitations on the present invention except as set forth in the appended claims. All parts and percentages are by weight unless otherwise specified.

EXPERIMENTAL

The examples herein were conducted according to the following general procedure. To a round bottom flask was added the desired mounts of the hydridosilyl reactant (or, following the less preferred mode of addition, the vinyl silyl reactant), noble metal catalyst and amine promoter under an atmosphere of nitrogen. The flask was equipped with a Friedrich ® condenser, a Vigreaux ® reflux column, and an addition funnel. The flask contents were heated to the desired temperature and the contents were stirred with a magnetic stirring bar. The vinyl silyl reactant (or, following the less preferred mode, the hydrido-silyl reactant) was slowly added using the addition funnel. Unless otherwise specified, the concentration of the Pt-catalyst was 20 ppm by weight based upon the total charge of reactants and was added as a 10% solution of chloroplatinic acid hexahydrate in a mixed solvent consisting of 90% dimethoxyethane and 10% ethanol. The addition of the vinyl silyl reactant generally required approximately 1 hour. Temperature was maintained between 100° C. to 110° C. for one hour following the completion of the addition of the vinyl silyl reactant. An aliquot was removed from the reaction flask and analyzed for SiH content by treatment with an alcoholic solution of potassium hydroxide as taught in The Analytical Chemistry of Silicones, Smith, A.L., Wiley-Interscience, New York (1991). If this test showed that essentially 100% of the SiH units had been consumed by the reaction, the reaction was deemed to be complete. Otherwise, heating was continued until the SiH content in the aliquots remained constant. The contents of the crude reaction were analyzed by gas chromatography and mass spectrometry. The concentrations were reported as weight percent.

Examples 1–8

Examples 1–8 were conducted according to the above procedure using the reactants, catalyst, and promoter set forth in Table 1 at the conditions and mode of addition set forth in Table 2. The results are described in Table 2. All these examples produced the desired product. Examples 1–8 show that the best overall results in terms of highest product yield and lowest vinyl-hydrogen exchange by-product yield are obtained in Example 3.

TABLE 1

REACTANTS FOR EXAMPLES 1–8

| Example Number | Hydridosilyl Reactant: $Me_3SiOSiHMeOSiMe_3$ | Vinyl Reactant: $(CH_2=CH)Si(OMe)_3$ | Platinum Catalyst | Promoter |
|---|---|---|---|---|
| 1 | 74.8 g (0.337 m)* | 52.9 (0.354 m) | 20 ppm Pt as 10% CPA Solution | None |
| 2 | 69.9 g (0.315 m) | 49.0 (0.331 m)* | 20 ppm Pt as 10% CPA Solution | None |
| 3 | 70.0 g (0.315 m) | 48.9 (0.331 m)* | 20 ppm Pt as 10% CPA Solution | 200 ppm PZ |
| 4 | 111.0 g (0.5 m)* | 78.5 (0.525 m) | 20 ppm Pt as 10% CPA Solution | 200 ppm PZ |
| 5 | 76.1 g (0.343 m)* | 53.9 g (0.360 m) | Pt—Vi Complex** | None |
| 6 | 70.4 g (0.317 m) | 49.8 g (0.333 m)* | 20 ppm Pt as 10% CPA | 0.005 g TPP |

TABLE 1-continued

REACTANTS FOR EXAMPLES 1-8

| Example Number | Hydridosilyl Reactant: Me$_3$SiOSiHMeOSiMe$_3$ | Vinyl Reactant: (CH$_2$=CH)Si(OMe)$_3$ | Platinum Catalyst | Promoter |
|---|---|---|---|---|
| 7 | 78.8 g (0.355 m) | 55.8 g (0.373 m)* | 20 ppm Pt as 10% CPA | None |
| 8 | 76.6 g (0.345 m) | 54.1 g (0.362 m)* | 20 ppm Pt as 4.9% solution of Pt(AcAc)$_2$ | None |

*Reactant fed to the flask
**1,2-divinyltetramethyldisiloxane-platinum complex (20 ppm Pt)

TABLE 2

HYDROSILATION OF ViSi(OMe)$_3$ WITH (Me$_3$SiO)$_2$SiMeH

| Ex. No. | Platinum Compound/ Promoter Pt. ppm** | Reactant Fed | Conditions Total Time, hrs. | Conditions Rxn Temp., °C. | Products, wt % Internal Prod #1 | Products, wt % Intended Prod #2 | Vinyl Redist. By-Products wt % Prod #3 | Vinyl Redist. By-Products wt % Prod #4 |
|---|---|---|---|---|---|---|---|---|
| 1 | CPA | SiH Comp | 1.75 | 90–118 | 8.85 | 59.8 | 4.60 | 9.16 |
| 2 | CPA | Vi Comp | 1.50 | 90–105 | 9.39 | 65.8 | 1.63 | 3.2 |
| 3 | CPA/200 ppm PZ | Vi Comp | 1.50 | 100–115 | 9.57 | 75.2 | 0.55 | 2.08 |
| 4 | CPA/200 ppm PZ | SiH Comp | 3.50 | 70–86 | 9.51 | 65.5 | 3.53 | 8.37 |
| 5 | Pt—Vi Complex | Vi Comp | 2.00 | 90–108 | 9.65 | 69.3 | 1.53 | 4.47 |
| 6 | CPA/TPP | Vi Comp | 1.50 | 87–100 | 8.32 | 61.5 | 1.23 | 1.88 |
| 7 | CPA/MeCN | Vi Comp | 1.50 | 92–110 | 8.99 | 64.0 | 2.29 | 3.81 |
| 8 | Pt(AcAc)$_2$ | Vi Comp | 2.50 | 85–120 | 10.68 | 58.5 | 3.20 | 6.24 |

Product
1 (MeO)$_3$SiCHMeSiMe(OSiMe$_3$)$_2$
2 (MeO)$_3$SiC$_2$H$_4$SiMe(OSiMe$_3$)$_2$
3 (MeO)$_3$SiC$_2$H$_4$Si(OMe)$_3$
4 (Me$_3$SiO)$_2$MeSiC$_2$H$_4$SiMe(Me$_3$SiO)$_2$
CPA = 10% Chloroplatinic Acid Solution
PZ = Phenothiazine
TPP = Tripheny phosphine
Pt(AcAc)2 = Acetylacetonate Complex of Pt
MeCN = Acetonitrile
Vi Comp = vinylic reactant
SiH Comp = hydridosilyl reactant
Pt—Vi Complex = 1,2-divinyltetramethyldisiloxane-platinum complex
*5% excess ViS(OMe)$_3$
**20 ppm of Pt used in all cases (measured as Pt)
Product/By-Product numbers are uncorrected area percents from GC analyses From Tables 1 and 2, it can be seen that Example 1 illustrates the preparation of a surface-active siloxane compound having a composition as defined by the present invention. The mode of addition of the reactants is the less preferred mode, i.e., the hydridosilyl reactant was added to the vinyl silyl reactant; nonetheless, a useful yield of the intended product was obtained.

It can be seen from the Tables that Example 2 illustrates the preferred mode of addition of reactants, which gives a higher yield of intended product than that obtained in Example 1. The preferred mode of addition is the addition of the vinyl silyl reactant to the hydridosilyl reactant.

Example 3 as set forth in Tables 1 and 2 illustrates the addition of a weakly complexing amine promoter to suppress vinyl-hydrogen exchange and increase the yield of intended product. The preferred mode of addition was used.

Example 4 illustrated the use of amine promoter which has the beneficial effect of suppressing vinyl-hydrogen exchange and increasing yield even when the less preferred mode of addition was used.

Example 5 illustrated the use of an alternative platinum catalyst to prepare a surface-active siloxane composition of the present invention.

From Example 6, it can be seen that a strongly complexing promoter, such as triphenylphosphine, is less effective than a weakly complexing promoter, such as phenothiazine, at increasing the yield of intended product and suppressing vinyl-hydrogen exchange.

Example 7 illustrated the effect of addition of acetonitrile, a strongly complexing nitrogen-containing promoter which coordinates to the platinum.

Example 8 shows the preparation of a composition of the present invention using a different platinum catalyst, one which contains two of the strongly complexing acetylacetonate groups. Although the intended product was obtained, demonstrating that this platinum catalyst effects the intended reaction, no increased yield was observed and vinyl-hydrogen exchange was not suppressed.

Example 9:

Preparation of 2-(1-heptamethylcyclotetrasiloxanyl) ethyltrimethoxysilane

This example illustrates the preparation of a cyclic surface-active siloxane compound as set forth in Formula II.

The apparatus for this experiment consisted of a 250 ml three neck flask equipped with an addition funnel, magnetic stirrer and Friedrich ® condenser. Under an atmosphere of nitrogen, 25 grams of vinyltrimethoxysilane was charged to the flask. This represented a 5% stoichiometric excess of the vinyl silyl reactant over the amount of the hydridosilyl reactant subsequently added to the reaction flask for the hydrosilation reaction. From the addition funnel was added approximately 5% by weight of the total charge of heptamethylcyclotetrasiloxane. With the reaction flask at 75° C., 20 ppm of Pt was added as a chloroplatinic acid solution (CPA). A substantial exotherm resulted and the reaction flask was cooled with ice water as the remainder of the SiH reactant was added. A total of 47.9 grams of heptamethylcyclotetrasiloxane (93.3% purity) was added over 15 minutes. Temperature was maintained at 85° C. for one hour. An analysis of an aliquot from the flask showed that more than 99% of the SiH reactant had reacted. The crude product contained:

4.9% of unreacted vinyltrimethoxysilane, 14% 1-(1-heptamethylcyclotetrasiloxanyl)ethyltrimethoxysilane and 77.4% of 2-(1-heptamethylcyclotetrasiloxanyl)-ethyltrimethoxysilane, as analyzed by gas chromatography and mass spectrometry.

Example 10:

Hydrosilation of Vinyltrimethoxysilane with Pentamethyldisiloxane

In accordance with the general procedure, the reaction flask contained 47.5 grams (0.321 moles) of pentamethyldisiloxane, 200 ppm (0.02 grams) of phenothiazine and 20 ppm Pt (added as a 10% CPA solution). A total of 49.84 grams (0.337 moles) of vinyltrimethoxysilane was slowly fed from the addition funnel. The reaction flask was maintained at 85° C. to 90° C. for 30 minutes. After the addition of the vinylsilane, the flask contents were heated to 98° C. for one hour. An aliquot taken showed that there was no detectable SiH in the crude product. The flask contents were analyzed by gas chromatography and mass spectrometry. The flask contained 3.76% unreacted vinyltrimethoxysilane, 19.0% of the internal addition by-product, $Me_3SiOSiMe_2CH(Me)Si(OMe)_3$ and 75.8% of the intended product, $Me_3SiOSiMe_2CH_2CH_2Si(OMe)_3$. Formation of vinyl-hydrogen exchange by-products was not observed.

Example 11:

Hydrosilation of Vinyltrimethoxysilane with tris (Trimethvlsiloxy)silane

In accordance with the general procedure the reaction flask contained 58.7 grams (0.198 moles) of tris(trimethylsiloxy)silane, 200 ppm of phenothiazine and 20 ppm of platinum (added as a 10% solution of CPA). From the addition flask was added 31.1 grams of vinyltrimethoxysilane. The reaction was exothermic. The initial reaction temperature was 86° C. and the final temperature was 118° C. After the addition, the temperature was maintained between 110° C. and 118° C. for 1.5 hours. Sequential aliquots indicated that residual SiH reactant remained at a constant amount. The crude product contained 12% unreacted vinyltrimethoxysilane, 26.2% unreacted tris(trimethylsiloxy)silane and 56.4% of the intended product, $(Me_3SiO)_3SiCH_2CH_2Si(OMe)_3$. Formation of vinyl-hydrogen exchange by-products was not observed.

Example 12:

Preparation of an Aqueous Emulsion of a Surface-Active Siloxane Compound

In a small flask fitted with a magnetic stirrer were combined 0.23 grams of Span 60 ® and 0.17 grams of Myrj 52S ® (Span 60 ® and Myrj 52S ® are fatty alcohol ethoxylate emulsifiers sold by ICI Americas, Inc.). The mixture of emulsifiers was stirred and warmed slightly until melted. A surface-active siloxane compound, (3-(triethoxy-silylethyl)heptamethyltrisiloxane), produced by the method of the present invention was added and stirred until homogeneous. Deionized water (7.6 grams) was added with vigorous stirring. A milky emulsion was formed. This example demonstrates that the surface-active siloxane compounds of the present invention can be converted to aqueous emulsions. The emulsion so prepared is applied to glass fibers by immersion. After drying, the fibers are hydrophobized as evidenced by little or no spreading of a droplet of water applied thereto.

Example 13:

Use of Surface Active Siloxane Compound for Water Repellency in Concrete

This example illustrates the effectiveness of the compounds of the present invention as waterproofing agents for concrete. Concrete tablets (2 inch diameter by 1 inch thick) were made by casting a concrete mix (prepared according to the directions on the packaging) in a Teflon ® coated muffin-shaped baking pan and followed by air drying at ambient temperature for 20 days. The concrete mix was commercially available as Sakrete ® from American Stone Mix, Inc., (Towson, Md). The tablets were immersed for 8 seconds in 200 grams of isopropyl alcohol solutions containing 20 weight percent of the silicone compounds listed in Table 3, followed by air drying at ambient temperature for 24 hours. The tablets were immersed for specified time periods in distilled water at ambient temperature such that the water level was one inch above the top of the tablets. After immersion, the tablets were wiped manually with paper towels. Individual weights of the dried concrete tablets were recorded after preparation, after silicone compound treatment, and after specific time periods of water immersion. Table 3 shows that (1) the silicon compound of the present invention is incorporated into the concrete tablets to a greater extent, and (2) the product of the present invention results in lower uptake of water from immersion than do alkylalkoxysilanes which are used commercially in water-repellent formulations.

TABLE 3

| Silicon Compound | Prepared Weight[b] | Weight Gain[c] | Water Take-up | | | | |
|---|---|---|---|---|---|---|---|
| | | | 24 hr | 48 hr | 72 hr | 144 hr | 168 hr |
| n-Propyl Si(OMe)$_3$ | 184.9 | 0.25 | 2.92 | 3.42 | 3.82 | 4.72 | 4.91 |
| Isobutyl Si(OMe)$_3$ | 207.1 | 0.32 | 2.80 | 3.36 | 3.79 | 4.78 | 4.99 |
| Amyl Si(OEt)$_3$ | 179.1 | 0.34 | 2.48 | 2.94 | 3.36 | 4.27 | 4.46 |
| n-Octyl Si(OEt)$_3$ | 209.5 | 0.55 | 3.66 | 4.47 | 4.91 | 5.66 | 5.76 |
| Example 3 | 187.6 | 0.71 | 2.05 | 2.56 | 2.96 | 3.90 | 4.08 |
| Controls[a,d] | 146.8 | 0.11[a] | 7.74 | 7.85 | 7.85 | 7.90 | 8.00 |

[a]No silicon compound; isopropyl alcohol only
[b]All weights in grams, average of two tablets
[c]From immersion for eight seconds in 20 weight-percent solution of silicon compound in isopropyl alcohol
[d]Average of three tablets

What is claimed is:

1. A siloxane compound having the general formula $(RO)_x R^1{}_{3-x}SiR^2SiX_yR^1{}_{3-y}$ or

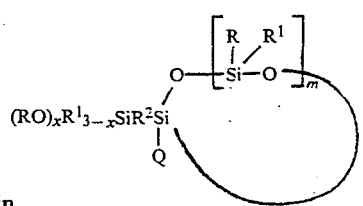

wherein
X is selected from the group consisting of
(i) —OSiR$_3$ and
(ii)

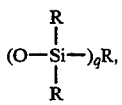

q has a value of 1 to 5;
R is an alkyl group having 1 to 6 carbon atoms;
R$^1$ is selected from the group consisting of
(i) an alkyl group having 1 to 6 carbon atoms;
(ii) an aryl group having 6 to 12 carbon atoms;
(iii) an aralkyl group having 7 to 13 carbon atoms; and
(iv) an alkaryl group having 7 to 13 carbon atoms;
R$^2$ is a linear or branched alkylene group having 2 to 12 carbon atoms;
Q is X or R$^1$ as defined herein; m has a value of 3 to 5; x has a value of 1 to 3; and y has a value of 2 to 3.

2. A siloxane compound according to claim 1 wherein R and R$^1$ are each methyl or ethyl groups, and R$^2$ is a linear or branched alkylene group having 2 or 3 carbon atoms, and x is 2 or 3.

3. A siloxane compound according to claim 1 selected from the group of $(Me_3SiO)_2SiMeC_2H_4Si(OMe)_3$, $(Me_3SiO)_3SiC_2H_4Si(OMe)_3$, $(Me_3SiO)_2SiMeC_2H_4Si(OEt)_3$, and

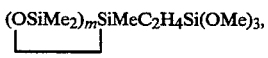

wherein m is 3 or 4; Me is a methyl group; and Et is an ethyl group.

4. A method of preparing a siloxane compound of claim 1 comprising reacting (a) a hydridosiloxane and (b) an alkenylalkoxysilane at a temperature ranging from about 50° C. to 150° C. in the presence of a noble metal catalyst and an amine promoter capable of forming a weak complex with the catalyst.

5. The method of claim 4, wherein the hydridosiloxane is selected from the group consisting of (i) a linear hydridosiloxane having the formula: $HSiX_yR^1{}_{3-y}$ and (ii) a cyclic hydridosiloxane having the formula:

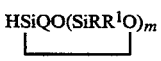

the alkenylalkoxysilane has the formula: $(RO)_xR^1{}_{3-x}SiZ$;
wherein in the hydridosiloxane and the alkenylalkoxysilane
X is selected from the group consisting of
(i) —OSiR$_3$ and
(ii)

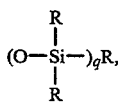

q has a value of 1 to 5;
R is an alkyl group having 1 to 6 carbon atoms;
R$^1$ is selected from the group consisting of
(i) an alkyl group having 1 to 6 carbon atoms;
(ii) an aryl group having 6 to 12 carbon atoms;
(iii) an aralkyl group having 7 to 13 carbon atoms; and
(iv) an alkaryl group having 7 to 13 carbon atoms;
Q is X or R$^1$ as defined herein;
Z is an alkenyl group having terminal unsaturation and having 2 to 4 carbon atoms; m is 3 to 5; x has a value of 1 to 3; and y has a value of 2 to 3. each x and y has a value ranging from about 1 to 3.

6. The method of claim 5 wherein the catalyst is selected from the group consisting of 1,2-divinyltetramethyl disiloxane complex of platinum, platinum bis(acetylacetonate), and chloroplatinic acid; the amine promoter is selected from the group consisting of phenothiazine, phenoxazine, diphenylamine, N,N'-diphenyl-p-phenylenediamine, and a carbon-alkylated derivative thereof; and wherein the alkenylalkoxysilane is added to the hydridosiloxane.

7. The method of claim 6 wherein the hydridosiloxane is selected from the group of $HSiMe(OSiMe_3)_2$, $HSi(OSiMe_3)_3$, and

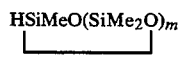

wherein m is 3 or 4; and Me is a methyl group.

8. A method of preparing a surface-active siloxane compound of claim 1 comprising reacting (a) a hydridoalkoxysilane and (b) an alkenylsiloxane at a temperature ranging from about 50° C. to 150° C. in the presence of a noble metal catalyst and an amine promoter.

9. The method of claim 8 wherein the hydridoalkoxysilane has the formula: $(RO)_xR^1{}_{3x}SiH$ and the alkenylsiloxane is selected from the group consisting of (i) a linear alkenylsiloxane having the formula: $ZSiX_yR^1{}_{3-y}$ and (ii) a cyclic alkenylsiloxane having the formula:

wherein in the hydridoalkoxysilane and the alkenylsiloxane
X is selected from the group consisting of
(i) —OSiR$_3$ and
(ii)

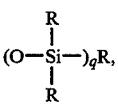

q has a value of 1 to 5;
R is an alkyl group having 1 to 6 carbon atoms;
R$^1$ is selected from the group consisting of
(i) an alkyl group having 1 to 6 carbon atoms;
(ii) an aryl group having 6 to 12 carbon atoms;

(iii) an aralkyl group having 7 to 13 carbon atoms; and (iv) an alkaryl group having 7 to 13 carbon atoms;

Q is X or $R^1$ as defined herein;

Z is a terminally unsaturated alkenyl group having 2 to 4 carbon atoms; m is 3 to 5; x has a value of 1 to 3; and y has a value of 2 to 3.

10. The method of claim 9 wherein the catalyst is selected from the group consisting of 1,2-divinyltetramethyl disiloxane platinum complex, platinum bis-(acetylacetonate), and chloroplatinic acid; the amine promoter is selected from the group consisting of phenothiazine, phenoxazine, diphenylamine, N,N'-diphenyl-p-phenylenediamine, and a carbon-alkylated derivative thereof; and wherein the alkenylsiloxane is added to the hydridoalkoxysilane.

* * * * *